United States Patent [19]

Whitsel

[11] 4,204,434
[45] May 27, 1980

[54] ULTRASONIC TESTING OF WELDS IN WHEELS

[75] Inventor: Jay F. Whitsel, Southampton, Pa.

[73] Assignee: The Budd Company, Troy, Mich.

[21] Appl. No.: 970,156

[22] Filed: Dec. 18, 1978

[51] Int. Cl.² ............................................. G01N 29/04
[52] U.S. Cl. ...................................................... 73/622
[58] Field of Search ................. 73/622, 620, 637, 640, 73/582

[56] References Cited

U.S. PATENT DOCUMENTS

| | | | |
|---|---|---|---|
| 3,266,300 | 8/1966 | Graboski | 73/637 |
| 3,554,029 | 1/1971 | Deininger | 73/620 |

*Primary Examiner*—Anthony V. Ciariante
*Attorney, Agent, or Firm*—A. L. Trueax, Jr.

[57] ABSTRACT

Methods and means for testing and storing data relating to the quality of resistance spot welds in an automotive wheel are provided. The wheel may be rotated for one revolution or less, dependent upon the number of transducers used, while a counter generates pulse signals representative of the locations of the wheel as it is revolved. Ultrasonic signals are transmitted towards and received from locations in the wheel at which the presence of welds is being tested. Storage devices, responsive to signals from the counter and the received ultrasonic signals store counts representative of the locations on the wheel where acceptable welds start and end to thereby determine the diameters of the welds. The data stored also indicate locations and durations of voids in the welded areas.

11 Claims, 3 Drawing Figures

FIG. 1
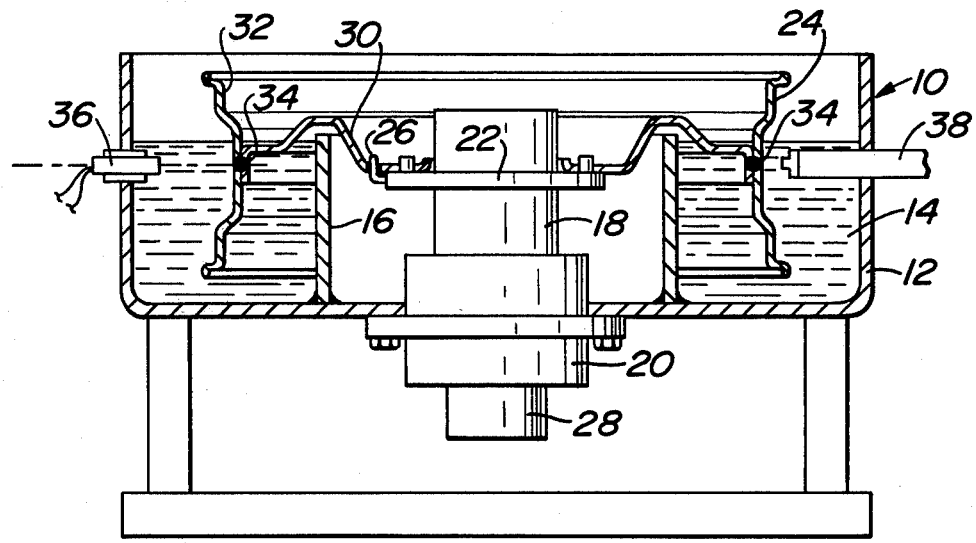
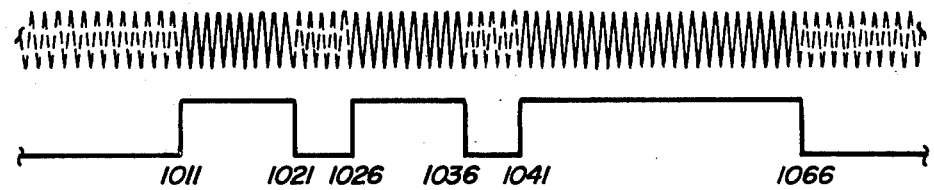
STORE COUNTS
FIG. 2

ULTRASONIC TESTING OF WELDS IN WHEELS

As is well known in ultrasonic inspection systems, a suitable transducer, such as a piezo electric crystal may be energized by short electrical pulse signals to cause the crystal to vibrate to produce mechanical waves of ultrasonic frequency which may be passed into the material being inspected. Reflected signals, which may involve multi echo signals, from the material under test may be received by the same transducer used for transmitting. Various circuits are then employed to evaluate the received signals. Water or other suitable transmission media is used between the transducer and the object under test to minimize energy loss during transmission and reception.

Because of the emphasis on safety, it is important that welds in automotive wheels be inspected before releasing them for assembly into an automobile. Due to the relatively large number of wheels involved in mass production, the means employed for inspection should be relatively fast, convenient and reliable.

Destructive methods have heretofore been used in determining the quality of wheels. Periodically, a sample wheel is exampled by generally destroying the wheel and visually observing the weld areas to determine the quality. This not only prohibits a high rate of inspection but is costly and time consuming.

An ultrasonic system for testing for the presence or absence of welds in disc brakes is described in a patent to Deininger U.S. Pat. No. 3,554,029, issued Jan. 12, 1971.

In checking for resistance spot welds in automotive wheels, it is often not sufficient to know welds have occurred in particular areas. It is necessary to know the diameter or width of the welds to determine their overall quality. Also, sometimes a weld having sufficient diameter include voids within the welds. If the voids are sufficiently large, the weld may be unacceptable.

It is an object of this invention to provide an improved system for testing the quality of welds in a wheel.

It is a further object of this invention to provide an improved system for testing the quality of welds in a wheel including detecting voids in an otherwise good welded area.

It is still a further object of this invention to provide an improved means for testing, storing and displaying data relating to the quality of welds in a wheel including the locations of the start and end of the diameter of each weld and any voids therein.

In accordance with the present invention, means and methods for testing welds in a wheel are provided. The wheel is placed in an oriented position on a fixture with the wheel being immersed in a liquid and then rotated for one or less revolution dependent upon whether one or a plurality of transducers are used. An encoder is connected to the fixture moving the wheel to produce output pulse signals as the wheel is rotated. These pulse signals are counted and multiplied. A transducer transmits and receives ultrasonic signals to and from the areas of the wheel being tested for welds. The locations of the start and end of ultrasonic signals, indicative of the presence of acceptable weld areas are stored as counts from the counter. The stored counts indicative of the diameters of the individual welds are suitably recorded or plotted.

Other objects and advantages of the present invention will be apparent and suggest themselves to those skilled in the art, from a reading of the following specification and claims, taken in conjunction with the accompanying drawing, in which:

FIG. 1 is a cross-sectional view of a typical automotive wheel on a fixture to be tested for weld quality, in accordance with the present invention;

FIG. 2 is a series of diagrams shown for purposes of explanation of the present invention; and, FIG. 3 is a block diagram, illustrating one form of the present invention.

Figure 3:
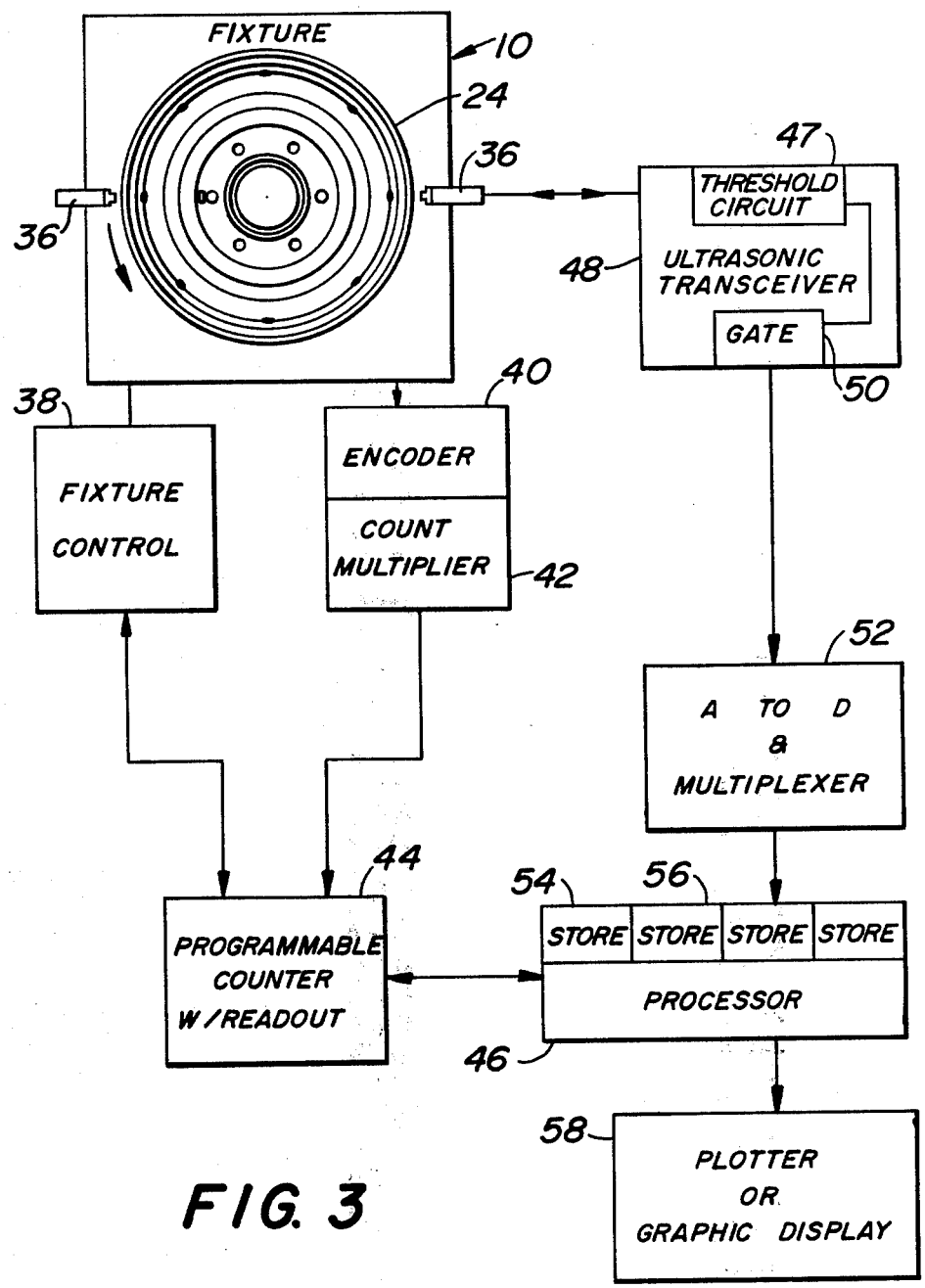

Referring particularly to FIG. 1, a fixture 10 comprises a container 12 having water, or other suitable liquid 14 therein. An inner circular partition 16 is connected to the bottom of the container 12 to provide a central portion free of water 14. A central rotating member 18 is adapted to be driven or rotated by a motor 20. The member 18 includes a circular support member 22 connected thereto. A wheel 24 to be tested is placed on the support member 22 and oriented by a tab 26 which extends through an opening in the wheel 24. Thus each time a wheel is installed to be tested, the precise location or starting point of the wheel is determined by the tab 26 and hole in the wheel.

A rotatable means comprising part of an encoder 40 (FIG. 3) is connected to the shaft of the motor 20. Means 28 rotates with the shaft of the motor and member 18 to generate electrical output pulse signals at the encoder 40 as the motor 20 is rotated. Such encoders are well known and, for example, may comprise an electric device which is turned off and on to generate pulse signals as a slotted plate moves with the shaft of the motor. When the wheel 24 is rotated, the encoder generates a predetermined number of pulse signals for each revolution, for example, 2500 pulses. The system is designed so that the wheel is rotated sufficiently to test all the weld areas involved. If a single transducer is used, the wheel will rotate one revolution and stop. If more than a single transducer is used, for example eight, the wheel would have to be rotated one eighth or less of a revolution sufficient to check all the weld areas.

The degree of rotation and stopping time of the wheel is controlled by a counter operative by signals from the decoder. Various limit switches may be included in the system if desired. Arrangements for stopping the wheel at the end of one or less revolution are known to those skilled in the art and are only incidentally related to the present invention and therefore not described in detail. For example, a stop pin could be actuated and inserted into an aperture in the wheel to stop the wheel at the desired time.

A typical automotive wheel may, for example, include eight resistance spot welds therein which mounts the center wheel portion 30 to the outer rim 32. The weld joints are illustrated by spot welds 34. Of course, the wheel may include more or less welds than eight. An ultrasonic transducer 36 extends through the outer wall of the container 12 and directed to transmit and receive ultrasonic signals to and from the spot weld areas provided at weld 34. The water 14 permits transmission of the ultrasonic signals without excessive attenuation. In order to assure that the welds 34 are at the proper height, an optical viewing pipe 38 may be provided. This permits an operator to optically view the wheel 24 to determine that the weld areas to be tested are at the proper heights. The optical viewing pipe 38 and the transducer 36 may be disposed at the same heights. Means, not illustrated may be employed to vary slightly the heights of the mechanism holding the wheel.

After the wheel 24 is inserted onto the fixture 10, the motor 20 is actuated and drives the wheel 24 for one revolution or less, dependent on the number of transducers used, at which time it stops. During the movement of the wheel, ultrasonic signals from the transducer 36 are transmitted and received to and from the weld areas of the wheel. While the testing of the wheel 24 requires one or less revolution, it is apparent that the wheel could be allowed to rotate after the testing procedure has been completed.

The present invention involves generally detecting the location of the start and end of the welds 34 as the wheel 24 is rotated. The start and end of the welds 34 is determined by the characteristics of the reflected signals as detected by the transducer 36. While the reflected signals are being received by the transducer 36, output count pulse signals are generated by the means 28 and multiplied as will be described. Each of these pulse signals generated in effect represent discrete locations on the wheels. For example, the encoder 40 including means 28 may be considered as representing 2500 locations on the rim of the wheel. The output signals from the transducer 36, representative of the presence or absence of welded areas, are utilized with the count signals to store the locations of wheel 24 where acceptable and non-acceptable welds occur. From the stored data, the individual and total weld width or diameters of the spot welds may be determined. For example, if the transducer 36 starts to detect a good weld, as determined by the reflected signals, a storage device or register stores the count signal from the decoder 40 and means 28. Likewise, at the end of a weld, as determined by the reflected signals, the count from the decoder (after multiplication) is stored in a register. The counts stored between the start and end of each weld may be read out of the storage registers to determine the diameters of the spot welds 34.

The reflected signals from the transducer 36 and from the means 28 are in effect combined in such a way so as to provide data relating to the diameter or width of the individual welds. If desired, the total widths of all of the spot welds in the wheel may be readily determined from the stored data. The stored data or information may now be compared with the specifications which must be complied with and which provide a standard to determine whether diameters of the spot welds in the wheel under test are acceptable or unacceptable. One of the features of the present invention is that, in addition to determining the diameter of the weld by storing data relating to the start and end of an acceptable weld area is that voids in the weld areas may be detected. If these voids are too great, it may indicate an unacceptable weld even though the diameter of the individual welds may be sufficient to indicate a good weld. Generally, although not necessarily, these voids are found towards the center of the weld area and involve irregular patterns.

Referring particularly to FIG. 2, the top waveform illustrates a series of equally spaced pulse signals which represents the output signals generated by means 28 and decoder 40 (FIG. 3), after the signals have been multiplied by four. For example, the 2500 cycles generated by the decoder would be stepped up from 2500 pulses, for example, to 10,000 equally spaced pulses per revolution. The increased number of pulses makes it possible to provide more accurate readings between the start and end of acceptable welds, as will be described.

The bottom waveform of FIG. 2 represents an idealized waveform representing a weld area which may be present in a wheel of a type which may be read out of storage visually displayed or plotted. The high amplitudes represent an acceptable weld area and the low amplitudes represent the absence of a weld or welds of unacceptable quality. For example, as the wheel 24 is rotated, the reflected output signals from the transducer 36 are indicated as being low when no or unacceptable welds are detected and high when acceptable welds are detected. In actual operation, however, the absence of welds may actually result in reflecting high signals and the presence of a weld may result in reflecting low signals. The reason for this is that welded joints will tend to attenuate received signals and reflect weaker echoes than a non-welded joint, which tends to reflect higher echo signals. However, this involves merely an inversion of the received signal and the waveform illustrated in FIG. 2 is idealized and merely intended to be representative of the waveform indicative of the different levels of signals reflected from the weld area.

Inversion circuits for inverting signals into some desirable form are well known. The important point is that a welded area will reflect different types of signals than a non-welded area and that these signals may be used in a conventional manner for gating and the like.

In the lower waveform of FIG. 2, it is noted that no output signal is recorded until an acceptable weld area is reached, at which point the signal raises at count 1011, for example. The signal remains high as long as an acceptable weld is present and may persist until count 1021, for example, as indicated by the solid line pulses. The period between the count 1021 and 1026, for example, may represent a void in the weld area or unacceptable weld levels indicated by dashed line pulses. At count 1026, for example, an acceptable weld is indicated by the high signal and continues until the count 1036, at which point it drops again to indicate a void. The void may continue until count 1041. At the count 1041, the signal then rises and continues to indicate an acceptable weld until the termination of the weld at count 1066. It is seen that the total weld time is represented by the time between count 1011 and 1066. Since the pulses represent integral distances on the wheel 24, the diameter or width of individual welds readily determined. At the same time, data relating to voids in what normally would be a good weld are indicated at particular count positions. If the area of the voids are too great or excessive in number the weld may be unacceptable even though the overall diameter of the weld may indicate otherwise.

In the system to be described in connection with FIG. 3, the method and means for storing and utilizing the various changes in signal levels at which the reflected signals from the transducer representing the start and end of acceptable weld areas are illustrated. The data relating to the count positions of the wheel during changes in signal levels are first stored and may be subsequently recorded or plotted. The stored data is then utilized to determine the diameters of the acceptable weld area of each of the individual welds as well as the total width of all the acceptable welds. After determining the diameter or width of each individual weld, if desired, the total width of all the welds are readily calculated in a processor or other device well known to those skilled in the art.

Referring particularly to FIG. 3, the wheel 24 under test within the fixture 10 is adapted to be rotated by the motor 20, as illustrated in FIG. 1. A fixture control unit 38 includes various switches and electrical circuits to control the various interconnections among the components illustrated. When the motor 20 is to be rotated, a switch or other means in the fixture control unit 38 is operated to start rotation of the motor 20 and the wheel 24. After one revolution or less, the motor 20 stops turning the wheel 24.

As the wheel 24 is turning, output signals are generated by the decoder 40 which is attached to respond to the positions of the shaft of the motor 24 (FIG. 1). As mentioned, for one revolution of the wheel 24, for example, the encoder 40 may generate 2500 pulse signals.

In order to increase the overall measurement accuracy, the signal from the encoder 40 is multiplied to 10000 cycles for example, by a count multiplier 42. Such multipliers are well known. A programmable counter with readout 44 receives the pulse signals from the count multiplier 42, which represent the discrete positions of the wheel 24 as it is rotated. The operation of the programmable counter 44 is controlled by various switches which may be included in the fixture control unit 38. The programmable counter 44 may be of the general type such as one manufactured by JMR Electronics Corporation, 1525 Brondell Ave., Bronx, N.Y. Such counters are capable of high counting rates and numerical readout. The output signals from such counters are storable in storage devices.

The output signals from the programmable counter 44 are applied to a processor 46. The processor 46 is capable of performing a number of computer operations including calculating, storing and comparing data. The programmable counter 44 as mentioned, is continuously indicating a count representative of the position of the wheel 24. The particular counts at which unacceptable and unacceptable weld areas occur are stored in storage devices within the processor 46.

As the wheel 24 is rotated, ultrasonic signals are applied between an ultrasonic transceiver 48 and transducer 36. The ultrasonic transducer 36 transmits and receives reflected signals from the weld areas. The transceiver 48 may be of a commercial type, for example a type sold under "MARK II" manufactured by Sonic Instrument Incorporated, 1018 White Head Road Extension, Trenton, N.J.

The ultrasonic transceiver 48 may include various threshold level controls, such as threshold circuit 47. As is well known, threshold levels may be set to respond to signals only below or above predetermined amplitudes. It is known that a welded joint tends to attenaute signals and will reflect less of a signal than a non-weld joint.

The reflected ultrasonic signals received by one or more transducers 36 are applied to the ultrasonic transceiver 48 pass through the threshold network 47. The output signals from the threshold circuit 47 are applied to a gate circuit 50. When signals applied to the threshold circuit 47 are below a predetermined threshold level the gate circuit 50 will open and pass a gating signal therethrough. The gate signal will be generated by the gate circuit 50 as long as the reflected signals to the transducer 36 indicates that a weld is at an acceptable level, as determined by the threshold circuit 47. When the reflected signals do not indicate an acceptable weld level, no signals will pass through the threshold circuit 47 and the gate circuit 50 will stay closed and no gate signals will be passed. The gate circuit 50 my be a Schmidt trigger or other similar type of bistable circuit.

In some cases, it is desirable to program the ultrasonic receiver 48 so that the search for weld areas take place only at selected counts from the counter where the weld joints are anticipated. Weld areas may in typical cases have diameters between one-half and three-quarter inches. In this case, it may be desirable to search in the weld zones which may comprise one inch. The locations of the weld areas are generally known. The operation, controlling and testing in only selected weld zones may be accomplished by processor 46. The output signals from the gate circuit 50 of the ultrasonic transceiver 48 are applied to an analog-to-digital converter and multiplexer unit 52.

The unit 52 converts the received signals into a digital form for acceptance by the processor 46. In some cases, a signal conditioner to handle various noise and other unpredictable undesired signals may be incorporated in the unit 52.

The output signal from the analog-to-digital converter and multiplexer 52 is applied to the processor 46 where it is combined with the output signals from the programmable counter 44. The processor 46 receives signals from the transducer 36 representing the start and end of a good weld on the wheel 24, as indicated by the signal from the gate circuit 50. The processor 46 also receives count signals from the programmable counter 44 and stores particular counts in storage devices or registers in the processor 46. For example, referring back to FIG. 2, the count representing the start of an acceptable weld may be stored in the storage device or register 54 as count 1011. Of course the register 54 is also controlled by the operating state of the gate circuit 50. At a later time when the weld signal indicates a void, that is at count 1021, the count 1021 may be stored in a storage device 56. Again the operating state of the gate 50 will determine when the end count is stored. As the weld signal continues, each of the changes indicating a change in amplitude positively or negatively is stored in a storage device of the processor 46. It is understood that a plurality of storage devices are indicated in the processor 46 for purposes of explanation and that such devices may take various forms, including circulating registers and the like.

All of the changes in levels of the weld signals are preferably stored in the processor 46. The various stored data relating to the count may be read out and put on a plotter or graphic display device 58 or other utilization device. An ink printer may print a waveform somewhat similar to that illustrated in the lower waveform of FIG. 2.

The system described permits resistance spot weld tests in automotive wheels formed by joining the rim to the disc to be inspected by a non-destructive method. The system may provide automatic wheel checks in line or on an automatic basis. The processor 46 stores data relating to each of the welds which data may be used for a variety of things. For example, each of the individual welds may be analyzed or the total welds may be analyzed.

It is recognized that various time delay circuits may be employed which would prevent the gate circuit 50 from opening or closing for very small voids or for signals outside of predetermined ranges. Generally the gate circuit 50 will be operated by average signal conditions persisting over some short time period.

In some cases involving an in-line inspection as mentioned, it may be desirable to provide a plurality of ultrasonic transducers. The processor then, through a scanning technique, may store information for each transducer output in a manner previously described.

Means may be provided, if desired to have indications or marks put on rejected parts or on acceptable weld portions of the wheels.

It is seen that the present invention provides methods and means for checking wheel welds without having to destroy the wheel and visually inspect the weld area.

What is claimed is:

1. A method of checking the diameters of spot welds in a wheel comprising the steps of:
   (a) placing the wheel in an oriented position on a fixture;
   (b) rotating said fixture with said wheels,
   (c) connecting a counter responsive to the rotation of said wheel to produce output electrical pulse signals representative of the positions of said wheel during rotation,
   (d) transmitting and receiving ultrasonic signals to and from said wheel as it is rotated,
   (e) producing a gate signal when the received ultrasonic signals are at threshold levels indicative of the presence an acceptable weld area in said wheel,
   (f) storing the counts from said counter at the start and end of said received ultrasonic signals indicative of the presence of said acceptable areas and,
   (g) utilizing the stored counts from said counter to provide indications of the diameters of said spot welds.

2. A method as set forth in claim 1 wherein the additional step is provided of immersing said wheel in a liquid prior to the rotation thereof.

3. A method as set forth in claim 2 wherein an additional step is provided of providing a plurality of transducers to transmit and receive said ultrasonic signals.

4. A method as set forth in claim 3 wherein said wheel is rotated less than one revolution when said plurality of transducers are used to check all the wheel areas in said wheel.

5. A method as set forth in claim 2 wherein the additional step is provided of utilizing the stored counts from said count to provide indications of voids in otherwise acceptable spot welds.

6. Means for testing weld areas in a wheel to determine the diameters thereof, comprising:
   (a) a fixture for receiving said wheels,
   (b) a motor for rotating said wheel,
   (c) a decoder connected to said motor to produce output signals when said wheel is rotated,
   (d) a counter responsive to the output signals from said decoder to produce pulse signals representative of the positions of said wheel during rotation,
   (e) a transducer for transmitting and receiving ultrasonic signals to and from said wheel while it is rotated,
   (f) a threshold level control circuit responsive to signals from said transducer,
   (g) a gate circuit responsive to signals from said threshold level control circuit to produce gate signals when the signals applied to said threshold level control circuit from said transducer are beyond predetermined threshold levels,
   (h) means for storing the counts from said counter at the start and end of said gating signals, and
   (i) means for utilizing data relating to said stored counts to determine the diameter of weld areas in said wheel.

7. Means for testing as set forth in claim 6 wherein means are provided to rotate said wheel one complete revolution to test all the weld areas in said wheel.

8. Means for testing as set forth in claim 6 wherein a plurality of transducers are provided for transmitting and receiving ultrasonic signals to said wheel and said wheel is rotated less than one revolution to test all the weld areas in said wheel.

9. Means for testing as set forth in claim 6 wherein means are provided to utilize data relating to said stored counts to indicate voids in normally acceptable weld areas.

10. Means for testing as set forth in claim 9 wherein a plotter is provided to indicate diameters and voids in acceptable weld areas.

11. Means for testing as set forth in claim 6 wherein an optical viewing pipe is disposed at the same height as said transducer on said fixture to optically view said weld areas.

* * * * *